(12) United States Patent
Cordatos

(10) Patent No.: US 11,340,186 B2
(45) Date of Patent: May 24, 2022

(54) METHOD FOR COMPOSITE WASTE REDUCTION

(71) Applicant: ROHR, INC., Chula Vista, CA (US)

(72) Inventor: Haralambos Cordatos, Colchester, CT (US)

(73) Assignee: ROHR, INC., Chula Vista, CA (US)

( * ) Notice: Subject to any disclaimer, the term of this patent is extended or adjusted under 35 U.S.C. 154(b) by 93 days.

(21) Appl. No.: 16/706,302

(22) Filed: Dec. 6, 2019

(65) Prior Publication Data

US 2021/0172894 A1    Jun. 10, 2021

Related U.S. Application Data

(60) Provisional application No. 62/797,020, filed on Jan. 25, 2019.

(51) Int. Cl.
*G01N 27/00* (2006.01)
*G01N 27/24* (2006.01)
*G01N 27/22* (2006.01)

(52) U.S. Cl.
CPC ........... *G01N 27/24* (2013.01); *G01N 27/221* (2013.01); *G01N 27/228* (2013.01)

(58) Field of Classification Search
CPC ..... G01N 27/24; G01N 27/221; G01N 27/228
See application file for complete search history.

(56) References Cited

U.S. PATENT DOCUMENTS

| 7,188,532 | B2 | 3/2007 | Goldfine et al. |
| 7,280,940 | B2 | 10/2007 | Goldfine et al. |
| 7,451,657 | B2 | 11/2008 | Goldfine et al. |
| 8,237,433 | B2 | 8/2012 | Goldfine et al. |
| 8,981,018 | B2 | 3/2015 | Goldfine et al. |
| 9,341,687 | B2 | 5/2016 | Donnangelo et al. |
| 9,575,014 | B2 * | 2/2017 | Leek ................ G01N 22/00 |

(Continued)

FOREIGN PATENT DOCUMENTS

| CN | 103698668 | 4/2014 |
| WO | 2018106194 | 6/2018 |

OTHER PUBLICATIONS

European Patent Office, European Search Report dated May 29, 2020 in Application No. 19216724.5.

(Continued)

*Primary Examiner* — Tung X Nguyen
*Assistant Examiner* — Feba Pothen
(74) *Attorney, Agent, or Firm* — Snell & Wilmer, L.L.P.

(57) ABSTRACT

A system for analyzing a state of a thermoset material is disclosed. In various embodiments, the system includes a source of electromagnetic energy configured to expose a sample of the thermoset material to an electric field; a detector configured to determine at least one of a dielectric permittivity or a complex admittance of the sample over a range of frequencies in response to a frequency sweep over the electric field; and an analyzer configured to assess the state of the thermoset material by comparing the at least one of the dielectric permittivity or the complex admittance of the sample against an acceptability map. In various embodiments, the acceptability map comprises a series of acceptability bands that represent a decrease in effective relaxation time from a baseline fresh batch of the thermoset material.

18 Claims, 5 Drawing Sheets

(56) References Cited

U.S. PATENT DOCUMENTS

2010/0066389 A1* 3/2010 Subramanyam ....... G01N 22/00
324/658
2018/0340900 A1* 11/2018 Reifsnider ........... G01N 27/221

OTHER PUBLICATIONS

Aishwarya Nandini et al: "Dielectric Property Investigation of Degraded Pre-Preg and Performance Prediction of the Final Composite Part", May 1, 2018 (May 1, 2018), XP055696712, Retrieved from the Internet: URL:https://www.researchgate.net/publication/326040947 [retrieved on May 19, 2020], pp. 1-12.

Alexandros A. Skordos et al: "Determination of the degree of cure under dynamic and isothermal curing conditions with electrical impedance spectroscopy", Journal of Polymer Science Part B: Polymer Physics, vol. 42, No. 1, Jan. 1, 2004 (Jan. 1, 2004), pp. 146-154.

Jovan Mijovic et al: "Application Note Dielectrics 2 Dielectric Spectroscopy of Reactive Polymers", Jan. 1, 1998 (Jan. 1, 1998), XP055696677, URL:http://novocontrol.de/pdf_s/APND2.PDF [retrieved on May 19, 2020], pp. 1-25.

Cristina Alvarez et al., "Relaxation Response of Polymers Containing Highly Flexible Side Groups Monitored by Boradband dielectric Spectroscopy," The Journal of Chemical Physics 122, pp. 194905-1 thru 194905-9, (2005).

Olivia De Andrade Raponi et al., "Development of a Single Dielectric Analysis Module for Online Cure Monitoring of a Commercial Epoxy Resin Formulation," Mechanical Engineering Institute and Information Technology and Systems Engineering Institute, Materials Research, Jul. 3, 2017, pp. 291-297.

Jovan Mijovic et al., "Dielectric Spectroscopy of Reactive Polymers," Department of Chemical Engineering, Chemistry and Materials Science, Polytechnic University, (1998) pp. 1-25, Novocontrol GmbH. Brooklyn, NY.

V. Komarov et al., "Permittivity and Measurements," Washington State University, Encyclopedia of RF and Microwave Engineering, Edited by Kai Change, ISBM 0-471-27053-9, (2005), pp. 3693-3711, John Wiley & Sons, Inc.

N. Axelrod et al., "Dielectric Spectroscopy Data Treatment: I Frequency Domain," Department of Applied Physics, Hebrew University of Jerusalem, Edmond Safra Campus, Givat-Ram, PII: SO957-0233(04)69473-2, (2004), Institute of Physics Publishing, Measurement and Technology vol. 15, pp. 755-764, Jerusalem, Israel.

A. Schonhals, "Dielectric Spectroscopy on the Dynamics of Amorphous Polymeric Systems," Novocontrol, Application Note Dielectrics 1, (1998), pp. 1-17, Novocontrol GmbH, Berlin, Germany.

* cited by examiner

METHOD FOR COMPOSITE WASTE REDUCTION

CROSS-REFERENCE TO RELATED APPLICATIONS

This application is a non-provisional application claiming priority to U.S. Prov. Appl. 62/797,020, entitled "METHOD FOR COMPOSITE WASTE REDUCTION," filed on Jan. 25, 2019, the entirety of which is hereby incorporated by reference herein for all purposes.

FIELD

The present disclosure relates generally to methods for determining a state of a material and, more particularly, to methods for determining a state of a resin.

BACKGROUND

Thermoset adhesives or resins used in the manufacture of composite structures are typically stored in cold environments (e.g., at or below −32° F. or 0° C.). The cold environments enable the internal structure and mechanical properties of such materials to maintain an integrity or suitability required for later use in the manufacture of the composite structures, at which time the materials are subjected to elevated temperatures necessary for curing. A shelf-life or expiration date of such materials is generally established based on an assumption that the materials will be stored at or below a specified temperature. Such time periods or dates, however, are typically arbitrary and overly conservative, leading to unnecessary disposal of otherwise satisfactory material (e.g., material having mechanical properties little changed from those of a fresh batch) merely because a shelf-life has expired or an expiration date has been reached. Methods and apparatus configured to rapidly and efficiently analyze the mechanical properties of thermoset adhesives or resins prior to or following an expiration date may provide substantial savings in the cost of replacing the materials and reductions in the premature disposal of otherwise acceptable quality materials.

Methods capable of assessing the state of thermoset materials currently exist, but these methods involve extensive, time-consuming laboratory testing by specialists and are thus not practical for use in manufacturing settings. For example, spectroscopic techniques such as infrared and Raman spectroscopy may nowadays be easily implemented, even with hand-held instruments. These techniques, however, rely on the formation of enough new chemical bonds to exceed their detection limit; and given the complexity of industrially relevant thermoset matrices, resolution of multiple overlapping peaks would be required. Moreover, it is unclear how exactly one would correlate any detectable changes in chemical bonding to changes in rheological and mechanical properties—especially in a resin matrix system that may contain many different materials: fibers (carbon, glass or aramid) and a range of additives such as curing agents, accelerators or flame retardants. Therefore, it is unlikely that monitoring changes in chemical bond formation via molecular spectroscopy may be used alone to determine the point at which a material has reached an unacceptable state. Other techniques, such as HPLC (High-Performance Liquid Chromatography), especially when used in conjunction with methods that monitor changes in glass transition temperature and mechanical properties, may be used to qualify the material with reasonable certainty, because they essentially assess, rather than infer, its state. However, their practice is time-consuming and requires a laboratory setting and specialized skills.

A practical approach to saving cost and reducing waste by preventing premature or unnecessary disposal of thermoset materials requires a simple-to-use technique that may be implemented quickly and accurately in a manufacturing environment. The following disclosure provides such an approach.

SUMMARY

A method of analyzing a state of a thermoset material is disclosed. In various embodiments, the method includes exposing a sample of the thermoset material to an electric field; performing a frequency sweep to determine at least one of a dielectric permittivity or a complex admittance of the sample over a range of frequencies; and assessing the state of the thermoset material by comparing the at least one of the dielectric permittivity or the complex admittance of the sample against an acceptability map.

In various embodiments, the acceptability map comprises a series of acceptability bands. In various embodiments, the series of acceptability bands represents a decrease in effective relaxation time from a baseline fresh batch of the thermoset material. In various embodiments, the series of acceptability bands comprises a real part of the at least one of the dielectric permittivity or the complex admittance. In various embodiments, the series of acceptability bands comprises an imaginary part of the at least one of the dielectric permittivity or the complex admittance.

In various embodiments, the electric field comprises a sinusoidal source signal. In various embodiments, the electric field comprises a pulse source signal. In various embodiments, the frequency sweep is performed at an isothermal condition. In various embodiments, the thermoset material is a prepreg material.

A method for analyzing a state of a thermoset material via a processor is disclosed. In various embodiments, the method includes exposing, via an emitter, a sample of the thermoset material to an electric field, the emitter being controlled by the processor; performing, via a detector, a frequency sweep to determine at least one of a dielectric permittivity or a complex admittance of the sample over a range of frequencies, the detector being controlled by the processor; and assessing, via the processor, the state of the thermoset material by comparing the at least one of the dielectric permittivity or the complex admittance of the sample against an acceptability map.

In various embodiments, the acceptability map comprises a series of acceptability bands. In various embodiments, the series of acceptability bands represents a decrease in effective relaxation time from a baseline fresh batch of the thermoset material. In various embodiments, the series of acceptability bands comprises a real part of the at least one of the dielectric permittivity or the complex admittance. In various embodiments, the series of acceptability bands comprises an imaginary part of the at least one of the dielectric permittivity or the complex admittance.

In various embodiments, the electric field comprises a sinusoidal source signal. In various embodiments, the electric field comprises a pulse source signal. In various embodiments, the frequency sweep is performed at an isothermal condition. In various embodiments, the thermoset material is a prepreg material.

A system for analyzing a state of a thermoset material is disclosed. In various embodiments, the system includes a source of electromagnetic energy configured to expose a sample of the thermoset material to an electric field; a detector configured to determine at least one of a dielectric permittivity or a complex admittance of the sample over a range of frequencies in response to a frequency sweep over the electric field; and an analyzer configured to assess the state of the thermoset material by comparing the at least one of the dielectric permittivity or the complex admittance of the sample against an acceptability map. In various embodiments, the acceptability map comprises a series of acceptability bands that represent a decrease in effective relaxation time from a baseline fresh batch of the thermoset material.

The forgoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1:
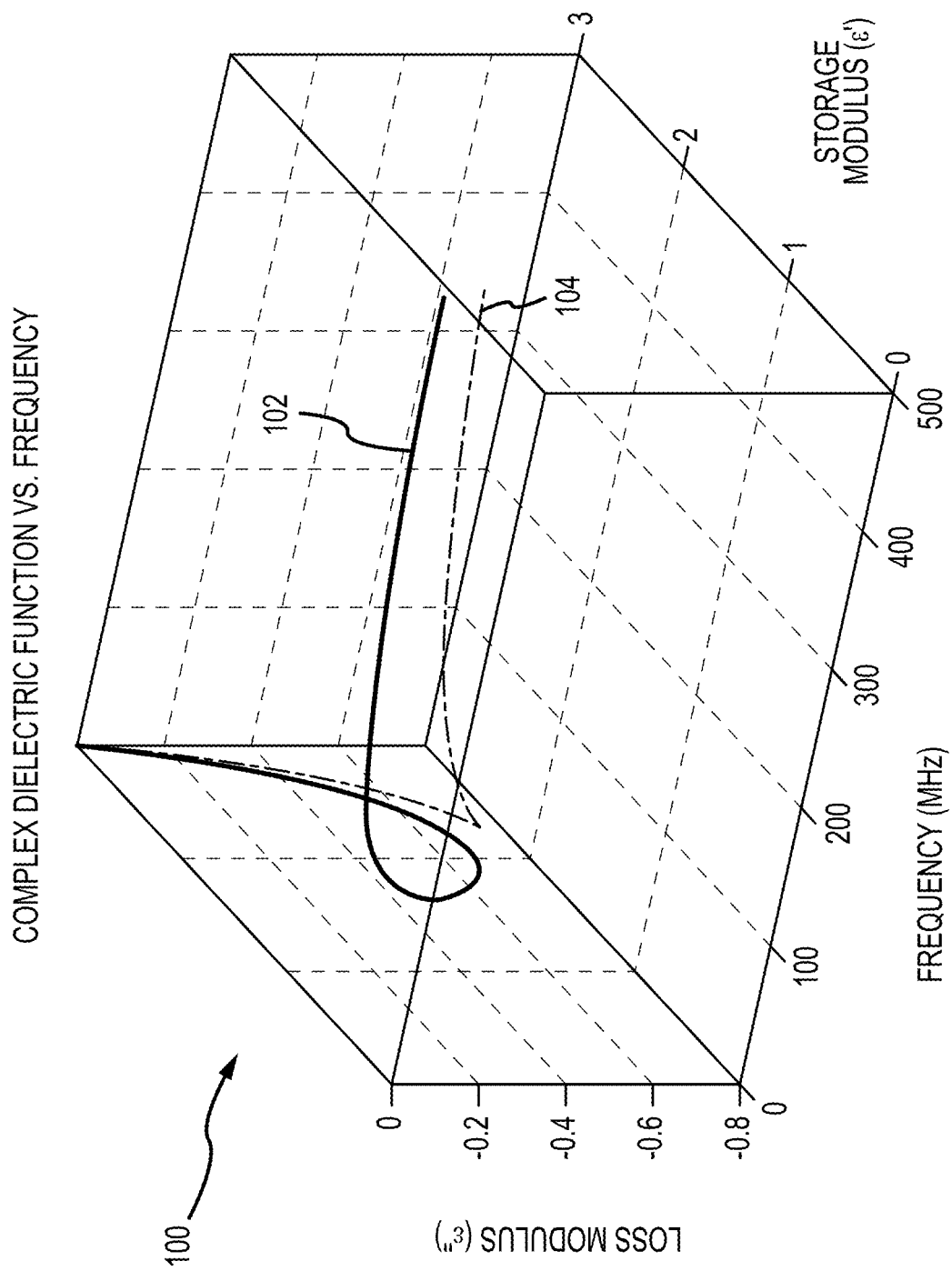
FIG. 1 is a plot of isothermal complex dielectric function versus frequency obtained for two relaxation times based on the Havriliak-Negami model, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

As a fresh batch of a thermoset adhesive progresses very slowly towards its cured state, all the changes taking place, whether detectable by molecular spectroscopy or not, ultimately lead to changes in the mobility of existing or induced dipoles (atomic or molecular) in the matrix. The origin of these changes may not be limited to formation of chemical bonds: any reorientation of molecular chains, due to relaxation or other reasons, may be a contributing factor. Therefore, probing the material with a technique sensitive to the changes in the average mobility of these dipoles is a promising approach. The methods disclosed herein may be rendered into a standard operating procedure that does not require expert supervision. The present disclosure is based on the realization that by collecting isothermal, complex dielectric permittivity versus frequency data from a resin or prepreg, one can derive essentially all the pertinent information related to changes in atomic, electronic and dipole relaxation properties, which in turn are correlated to what constitutes "early" versus "advanced" curing stages.

The complex, isothermal dielectric permittivity of a material exposed to an electric field may be defined as:

$$\varepsilon^*(\omega) = \varepsilon'(\omega) - i\varepsilon''(\omega) \quad (1)$$

where the real part, $\varepsilon'(\omega)$, is the storage modulus and the imaginary part, $\varepsilon''(\omega)$, is the loss modulus; and $\omega$ is the angular frequency of the electric field. In mathematical terms, this fundamental equation is the transfer function describing the response of a dielectric material to an electric field; for a sinusoidal input field, the storage modulus is the amplitude and the loss modulus is the phase change of the output respectively. Since dipoles, pre-existing or induced, interact with an externally imposed electric field, any changes in atomic, electronic or dipole relaxation properties of a thermoset resin will have an effect on $\varepsilon'(\omega)$, $\varepsilon''(\omega)$, or both at a given frequency range. In early stages of cure, when the dipolar relaxation dynamics are at the order of picoseconds, the changes in dielectric permittivity manifest themselves at GHz frequencies; in later stages of cure, when molecular weight and glass transition temperature increase towards gelation, the changes in dielectric permittivity manifest themselves at lower frequencies. Hence, knowledge of $\varepsilon^*(\omega)$ over a wide enough frequency range may be translated into knowledge of the combined impact of all the dipole relaxation, chemical bond formation and local reorientation related changes compared to an initial state of a fresh batch of material, even though the exact mechanisms may be unknown and undetectable. This impact may be within the threshold of the sensitivity of dielectric spectroscopy. However, the setup and methodologies used may be complex and geared toward in-depth understanding of the underlying phenomenological mechanisms rather than implementation as a simple quality assessment tool.

In order to demonstrate a procedure one might use to leverage dielectric spectroscopy for assessing the quality of a nearly-expired or expired thermoset material, a simple case of a material is assumed that can be modeled with a single dipole relaxation time, $\tau_m$. Its complex, isothermal dielectric constant may be described by the Havriliak-Negami relationship:

$$\varepsilon^*(\omega) = \varepsilon_\infty + \frac{\varepsilon_s - \varepsilon_\infty}{[1 + (i\omega\tau_m)^\alpha]^\beta} \quad (2)$$

where $\alpha$ and $\beta$ are empirical parameters, $0 \leq \alpha$, $\beta \leq 1$; and $\varepsilon_\infty$ and $\varepsilon_S$ are the limits of the dielectric constant at high and low frequency, respectively. This simple model may be inadequate to capture the frequency dependence of the complex dielectric constant of a real thermoset such as a composite prepreg; however, for demonstration purposes, the graph presented in FIG. 1 provides a useful illustration 100: it shows two curves (a first curve 102 and a second curve 104) obtained from equation (2) for two separate relaxation times and arbitrarily picked parameters $\alpha=0.8$ and $\beta=0.9$ (frequency $f=2\pi\omega$).

Figure 2:
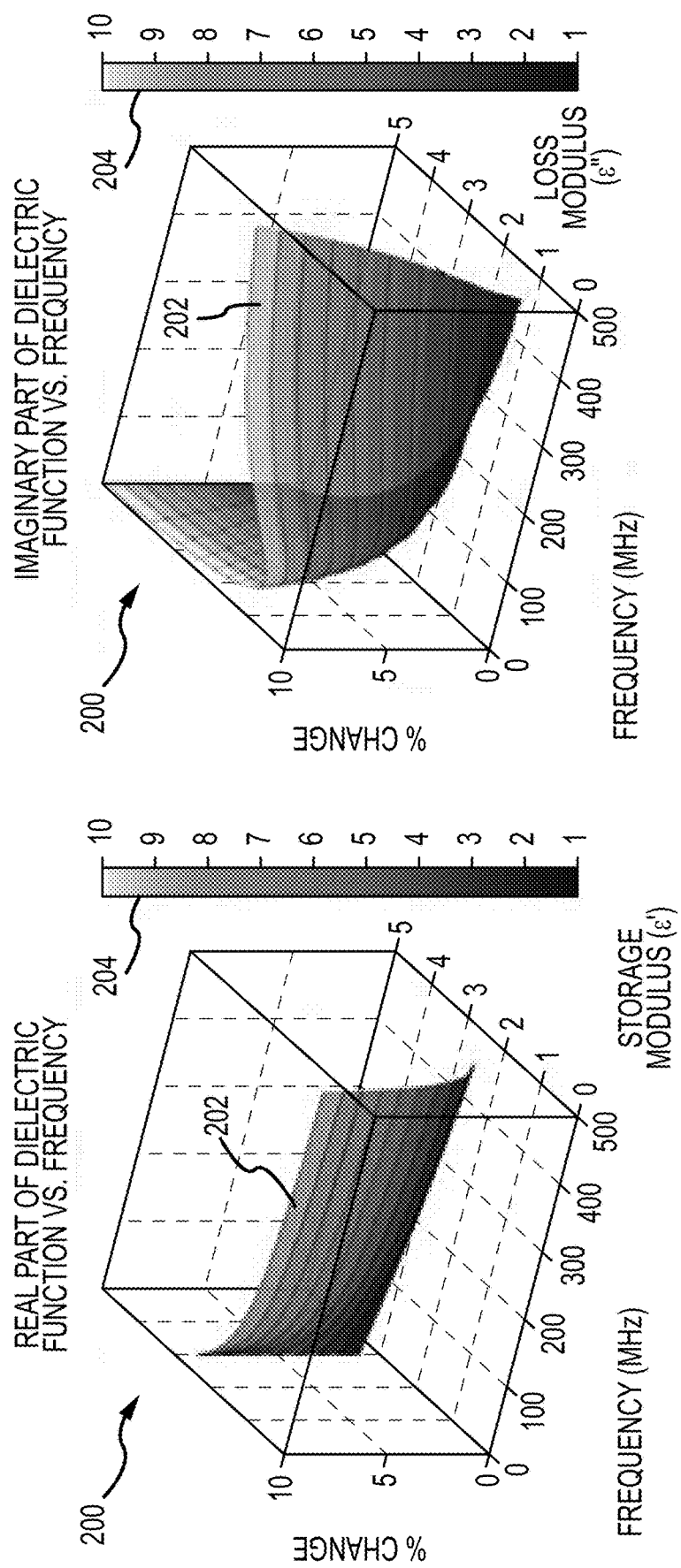
FIGS. 2A and 2B illustrate acceptability bands of a hypothetical thermoset based on changes in isothermal dielectric function signature, in accordance with various embodiments.

It is evident from this simple model that changes in dipolar relaxation dynamics are reflected into changes in the shape of the curve representing the dielectric permittivity function. By assuming, for example, as the thermoset material becomes more rigid over time, the effective relaxation time decreases; and that materials that exhibit >9-10% decrease in relaxation time are no longer acceptable. By depicting the changes in the real and imaginary parts of the dielectric permittivity, the surfaces shown in FIGS. 2A and 2B could be viewed as an "acceptability map" 200: for a given sample under consideration, experimental determination of its dielectric permittivity with a simple frequency sweep at isothermal conditions is translated into a % deviation from the baseline "fresh batch" and, in turn, a placement into a band 202 within the acceptability map 200, as represented by the shaded bars 204, which depict a percent deviation from the baseline "fresh batch" ranging from 1-10%. In other words, a given material's experimentally observable dielectric function "signature" is translated into (and may now be visualized as) an objective quality assessment regarding its suitability for further processing. For example, as described further below, the dielectric function of a given material may be experimentally determined. Once determined, the dielectric function of the material is compared against the acceptability map 200. If the percent change of the real or imaginary part of the dielectric function obtained experimentally is greater than, for example, a threshold value equal to 9 or 10% of the comparable values of dielectric function in the acceptability map, then the given material may be determined to have reached an expired state. If less than the threshold value, the given material may be determined to not have reached an expired state and to have a remaining shelf-life.

Figure 3:
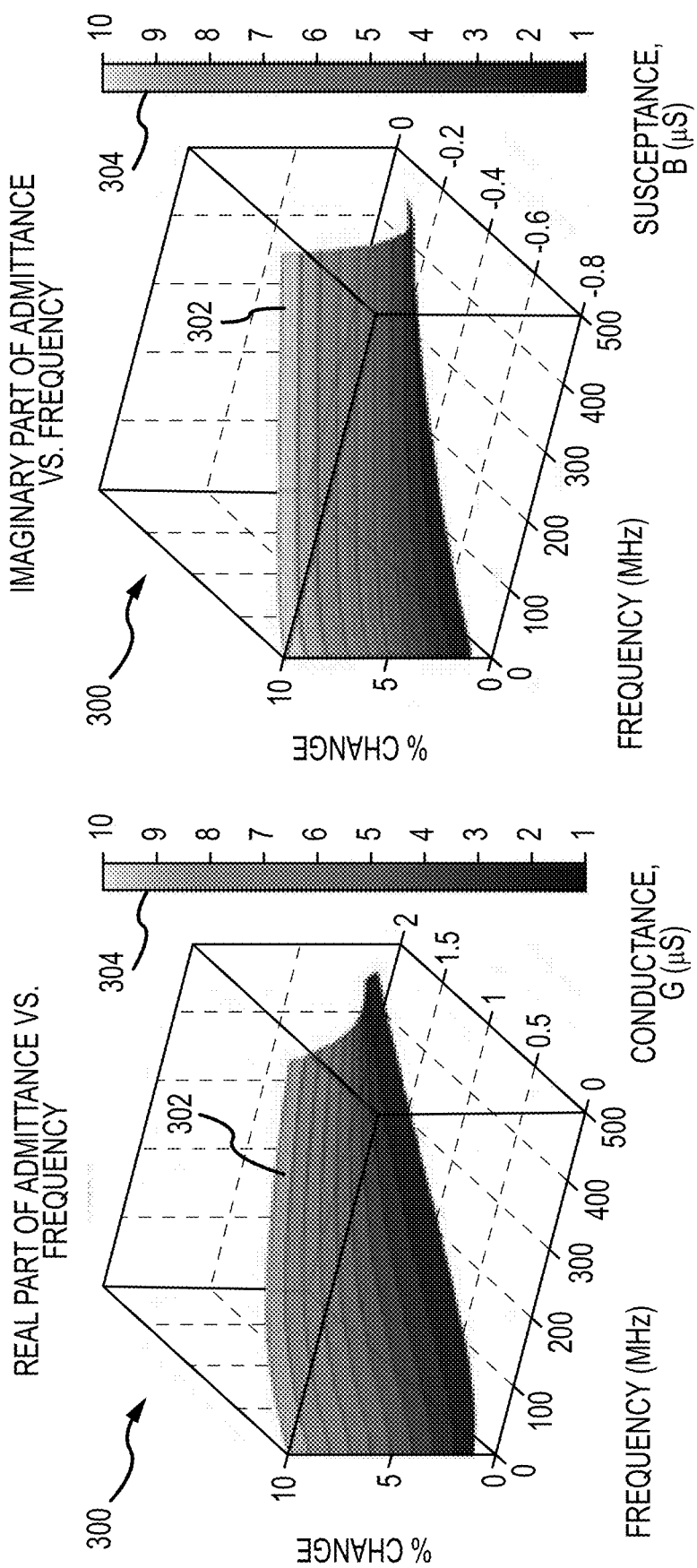
FIGS. 3A and 3B illustrate acceptability bands of a hypothetical thermoset based on changes in isothermal complex conductivity signature, in accordance with various embodiments.

In practice, determination of the frequency-dependent dielectric permittivity may be carried out in either the frequency domain or in the time domain. In the former, the material is subjected to a source signal (typically sinusoidal) and the material's response is detected in a frequency sweep, as outlined above. In the latter, the material is subjected to a step or pulse source signal and the reflected or transmitted signal is detected via a fast sampler. It can be shown that both methods are equivalent, each having pros and cons related to instrumentation, cost, etc. Using the same simple Havriliak-Negami model as the above example, and assuming that a manufacturing plant has determined that the most cost-effective and convenient approach for a certain thermoset is to measure its complex admittance (conductivity) in the frequency domain (e.g., the input signal is a sinusoidal voltage sweep and the output signal is the measured current). The complex conductivity is linked to the complex dielectric permittivity by:

$$\sigma^*(\omega) = i\omega\varepsilon_{vac}\varepsilon^*(\omega) \quad (3)$$

where $\varepsilon_{vac}$ is the vacuum permittivity (8.85e-12 F/m). Therefore, the changes in the real and imaginary part of the measured complex admittance may be depicted by the surfaces shown in FIGS. 3A and 3B. The "acceptability map" 300 is now obtained directly by sensing an experimentally measured parameter (admittance) that corresponds to a fundamental material property (permittivity). Similar to the dielectric permittivity described above, for a given sample under consideration, experimental determination of its complex admittance with a simple frequency sweep at isothermal conditions is translated into a % deviation from the baseline "fresh batch" and, in turn, a placement into a band 302 within the acceptability map 300, as represented by the shaded bars 304, which also depict a percent deviation from the baseline batch ranging from 1-10%.

The admittance of a material may be accessed by reference to either the real part or the imaginary part of the admittance, which are referred to, respectively, as the conductance and the susceptance (both measured in units of seimens). Generally speaking, conductance and susceptance are measures of the ease with which an electrical current passes through a material (e.g., the inverse of electrical resistance). Similar to the discussion of dielectric permittivity above, the admittance of a given material may be experimentally determined. Once determined, the admittance of the material is compared against the acceptability map 300. If the percent change of the real or imaginary part of the admittance obtained experimentally is greater than, for example, a threshold value equal to 9 or 10% of the comparable values of admittance in the acceptability map, then the given material may be determined to have reached an expired state. If less than the threshold value, the given material may be determined to not have reached an expired state and to have a remaining shelf-life.

In reality, the complex dielectric permittivity of a thermoset matrix would not be a simple function of a single relaxation time as depicted in equation (2) but rather an unknown function $G(\tau)$ that comprises instead a distribution of relaxation times. Hence, for the most general case:

$$\varepsilon^*(\omega) = \varepsilon_\infty + (\varepsilon_s - \varepsilon_\infty)\int_0^\infty \frac{G(\tau)}{1 + i\omega\tau}d\tau \quad (4)$$

where $\int_0^\infty G(\tau)d\tau = 1$. The methodology described above is still applicable, albeit the form of $G(\tau)$ may no longer be assumed to be the simple model and instead must be determined experimentally. To that end, conventional and novel mathematical techniques may be used to estimate the parameters of a function assumed to be a nonlinear superposition of relaxation times based on a "penalized maximum likelihood approach" applied to experimental data. Alternatively, recent advances in "supervised learning" algorithms (more widely known for applications in machine learning) may be more straightforward for generating reasonable predictions in this particular problem. For example, a technique known as SVM (Support Vector Machine) may be used to classify experimental dielectric permittivity data, separating them by a "hyperplane" (in simple terms, a decision boundary indicating whether the collected data fits the profile of an "acceptable" versus an "unacceptable" material). The latter approach may be the most preferable for a manufacturing environment, regardless of the complexity of the material itself and the algorithm used for its dielectric analysis, the ultimate result is a simple "acceptable/unacceptable" classification or perhaps a few percentage acceptability bands (similar to those shown in FIGS. 2A and 2B and FIGS. 3A and 3B) that can be immediately interpreted by an operator following a single experiment.

Figure 4:
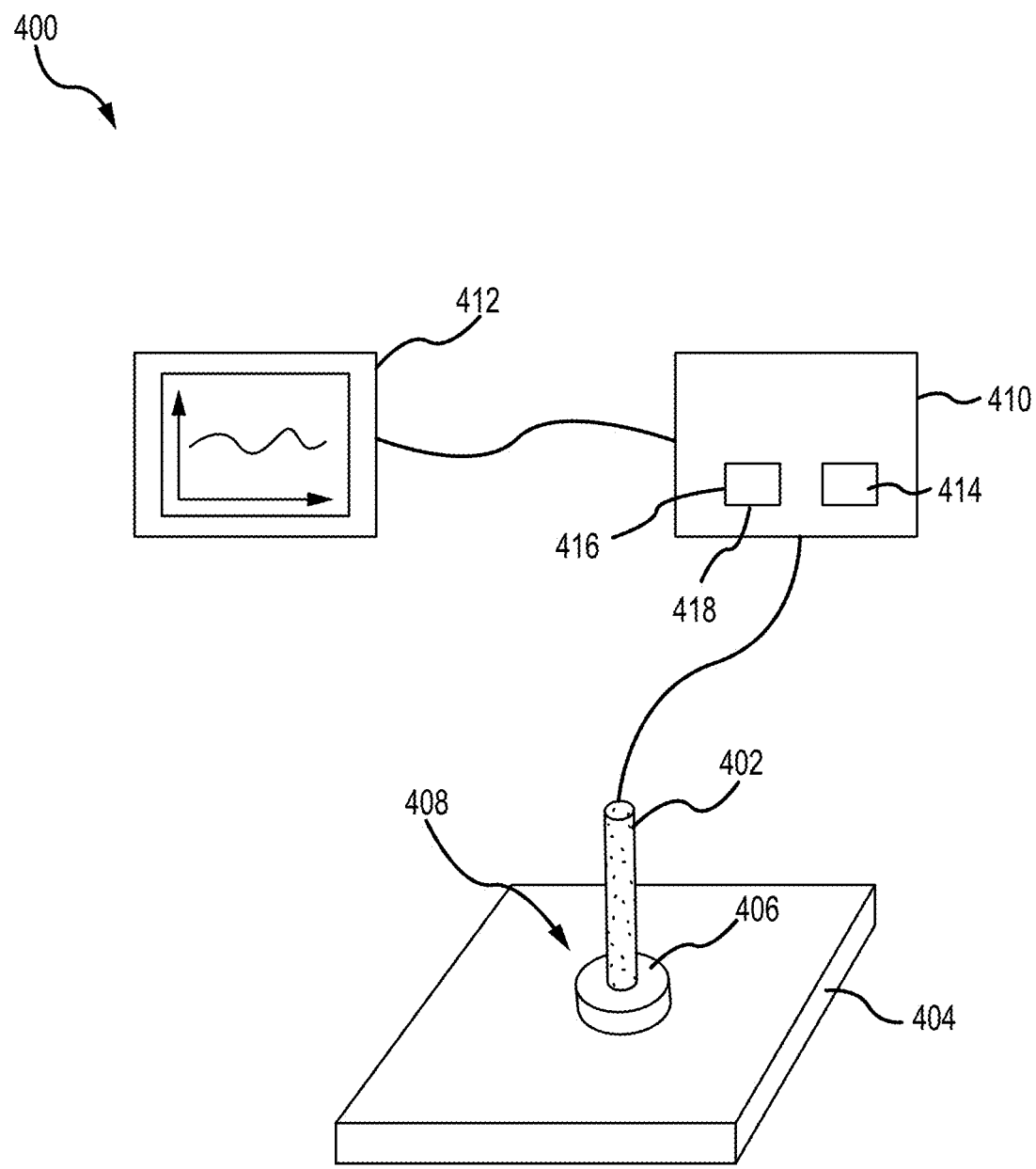
FIG. 4 illustrates a system configured for analyzing a state of a thermoset material, in accordance with various embodiments.

Referring now to FIG. 4, a system 400 for analyzing a state of a thermoset material is illustrated. In various embodiments, the system 400 includes a source of electromagnetic energy 402 (e.g., an emitter) configured to expose a sample 404 of the thermoset material to an electric field. The system 400 further includes a detector 406 configured to determine at least one of a dielectric permittivity or a complex admittance of the sample 404 over a range of frequencies in response to a frequency sweep over the electric field. In various embodiments, the source of electromagnetic energy 402 and the detector 406 may comprise a probe 408 or similar single combined unit that is easily manipulated against a surface of the sample 404. The system 400 further includes a processor 410 and, in various embodiments, an output device 412 (e.g., a computer or mobile device having a screen) configured to provide data to a user, the data being indicative of the state of the thermoset material. The processor 410 is configured to control the system 400, including, for example, operation of the source of electromagnetic energy 402 and the detector 406.

In various embodiments, the processor 410 includes one or more memories 414 (e.g., tangible, non-transitory memories) capable of implementing digital or programmatic logic. In various embodiments, for example, the processor 410 comprises one or more of a general purpose processor, a digital signal processor (DSP), an application specific integrated circuit (ASIC), a field programmable gate array (FPGA), or other programmable logic device, discrete gate, transistor logic, or discrete hardware components, or any various combinations thereof. The one or more memories 414 is configured to store instructions that are implemented by the processor 410 for performing various functions. The memories may also be configured to store one or more acceptability maps, such as the acceptability maps described above with reference to FIGS. 2A, 2B, 3A and 3B. The processor 410 may further include hardware 416 capable of performing various logic using data received from the detector 406 or the probe 408. For example, an analyzer 418 or similar hardware is configured to assess the state of the thermoset material by comparing the at least one of the dielectric permittivity or the complex admittance of the sample 404 against an acceptability map, such as one of the acceptability maps described above with reference to FIGS. 2A, 2B, 3A and 3B.

Figure 5:
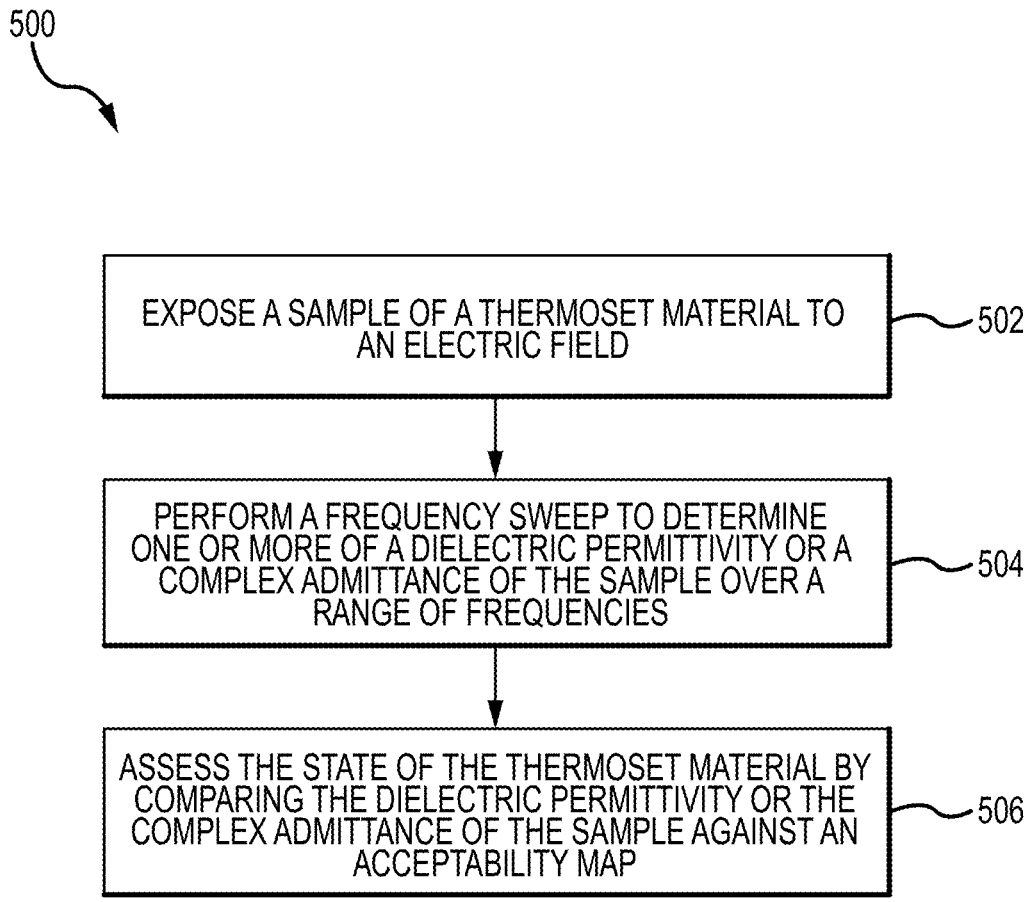
FIG. 5 describes a method of analyzing a state of a thermoset material, in accordance with various embodiments.

Referring now to FIG. 5, a method 500 of analyzing a state of a thermoset material is described as comprising the following steps. A first step 502 includes exposing a sample of the thermoset material to an electric field. A second step 504 includes performing a frequency sweep to determine one or more of a dielectric permittivity or a complex admittance of the sample over a range of frequencies. A third step 506 includes assessing the state of the thermoset material by comparing the dielectric permittivity or the complex admittance of the sample against an acceptability map. In various embodiments, the acceptability map comprises a series of acceptability bands that represent a decrease in an effective relaxation time from a baseline fresh batch of the thermoset material. In various embodiments, the acceptability map includes a series of acceptability bands that represent a decrease in effective relaxation time from a baseline fresh batch of the thermoset material. The series of acceptability bands comprises one or both of a real part and an imaginary part of the dielectric permittivity or the complex admittance. In various embodiments, the electric field comprises a sinusoidal source signal or a pulse source signal. In various embodiments, the frequency sweep is performed at an isothermal condition. In various embodiments, the method is configured to assess the state of a prepreg material, a resin or an adhesive.

Benefits, other advantages, and solutions to problems have been described herein with regard to specific embodiments. Furthermore, the connecting lines shown in the various figures contained herein are intended to represent exemplary functional relationships or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above described concepts can be used alone or in combination with any or all of the other above described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed:

1. A method of analyzing a state of a prepreg thermoset material, comprising:
exposing a sample of the prepreg thermoset material to an electric field;
performing a frequency sweep to determine at least one of a dielectric permittivity or a complex admittance of the sample over a range of frequencies;
assessing the state of the prepreg thermoset material by comparing the at least one of the dielectric permittivity or the complex admittance of the sample against an acceptability map; and
determining whether the at least one of the dielectric permittivity or the complex admittance is greater than or less than a threshold value of the acceptability map, thereby indicating whether or not the prepreg thermoset material has reached an expired state,
wherein the acceptability map indicates a percent deviation in the dielectric permittivity or the complex admittance, from a baseline fresh batch of the prepreg thermoset material, as a function of frequency.

2. The method of claim 1, wherein the acceptability map comprises a series of acceptability bands.

3. The method of claim 2, wherein the series of acceptability bands represents a decrease in effective relaxation time from the baseline fresh batch of the prepreg thermoset material.

4. The method of claim 3, wherein the series of acceptability bands comprises a real part of the at least one of the dielectric permittivity or the complex admittance.

5. The method of claim 3, wherein the series of acceptability bands comprises an imaginary part of the at least one of the dielectric permittivity or the complex admittance.

6. The method of claim 1, wherein the electric field comprises a sinusoidal source signal.

7. The method of claim 1, wherein the electric field comprises a pulse source signal.

8. The method of claim 1, wherein the frequency sweep is performed at an isothermal condition.

9. A method for analyzing a state of a prepreg thermoset material via a processor, comprising:
exposing, via an emitter, a sample of the prepreg thermoset material to an electric field, the emitter being controlled by the processor;
performing, via a detector, a frequency sweep to determine at least one of a dielectric permittivity or a complex admittance of the sample over a range of frequencies, the detector being controlled by the processor;
assessing, via the processor, the state of the prepreg thermoset material by comparing the at least one of the dielectric permittivity or the complex admittance of the sample against an acceptability map; and
determining, via the processor, whether the at least one of the dielectric permittivity or the complex admittance is greater than or less than a threshold value of the acceptability map, thereby indicating whether or not the prepreg thermoset material has reached an expired state,
wherein the acceptability map indicates a percent deviation in the dielectric permittivity or the complex admittance, from a baseline fresh batch of the prepreg thermoset material, as a function of frequency.

10. The method of claim 9, wherein the acceptability map comprises a series of acceptability bands.

11. The method of claim 10, wherein the series of acceptability bands represents a decrease in effective relaxation time from the baseline fresh batch of the prepreg thermoset material.

12. The method of claim 11, wherein the series of acceptability bands comprises a real part of the at least one of the dielectric permittivity or the complex admittance.

13. The method of claim 11, wherein the series of acceptability bands comprises an imaginary part of the at least one of the dielectric permittivity or the complex admittance.

14. The method of claim 9, wherein the electric field comprises a sinusoidal source signal.

15. The method of claim 9, wherein the electric field comprises a pulse source signal.

16. The method of claim 9, wherein the frequency sweep is performed at an isothermal condition.

17. A system for analyzing a state of a prepreg thermoset material, comprising:
a source of electromagnetic energy configured to expose a sample of the prepreg thermoset material to an electric field;
a detector configured to determine at least one of a dielectric permittivity or a complex admittance of the sample over a range of frequencies in response to a frequency sweep over the electric field; and
an analyzer configured to assess the state of the prepreg thermoset material by comparing the at least one of the dielectric permittivity or the complex admittance of the sample against an acceptability map and determining whether the at least one of the dielectric permittivity or the complex admittance is greater than or less than a threshold value of the acceptability map, thereby indicating whether or not the prepreg thermoset material has reached an expired state,
wherein the acceptability map indicates a percent deviation in the dielectric permittivity or the complex admittance, from a baseline fresh batch of the prepreg thermoset material, as a function of frequency.

18. The system of claim 17, wherein the acceptability map comprises a series of acceptability bands that represent a decrease in effective relaxation time from the baseline fresh batch of the thermoset material.

* * * * *